United States Patent
Murray

[11] Patent Number: 5,912,311
[45] Date of Patent: Jun. 15, 1999

[54] OLEFIN POLYMERIZATION METHOD COMPRISING ALLYL-CYCLOALKADIENYL DIANIONS AS CATALYST PRECURSORS

[75] Inventor: Rex Eugene Murray, Cross Lanes, W. Va.

[73] Assignee: Univation Technologies, LLC

[21] Appl. No.: 08/883,074

[22] Filed: Jun. 26, 1997

Related U.S. Application Data

[62] Division of application No. 08/536,947, Sep. 29, 1995, Pat. No. 5,700,748.

[51] Int. Cl.[6] ..................................................... C08F 4/44
[52] U.S. Cl. ................... 526/160; 526/131; 526/170; 526/171; 526/134; 502/117
[58] Field of Search ............... 526/90, 170, 171, 526/160

[56] References Cited

U.S. PATENT DOCUMENTS

| | | | |
|---|---|---|---|
| 3,422,128 | 1/1969 | Wilke et al. | 260/439 |
| 3,475,471 | 10/1969 | Maxfield | 260/429 |
| 5,081,231 | 1/1992 | Stevens et al. | 534/11 |
| 5,395,811 | 3/1995 | Novak et al. | 502/152 |

*Primary Examiner*—Jeffery T. Smith
*Assistant Examiner*—Roberto Rabago
*Attorney, Agent, or Firm*—C. L. Bell; J. Sher

[57] ABSTRACT

A catalyst precursor of the formula:

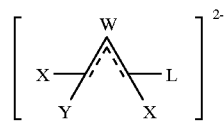

wherein:

L is a cycloalkadienyl ligand;

W, X, Y, and Z are independently hydrogen, a hydrocarbyl group containing 1 to 20 carbon atoms, or a silyl group, and may be connected to L through a bridging group comprising at least two Group IVA atoms; with the proviso that one of X, Y, and Z is a negative charge stabilizing group selected from the group consisting of Group IVA trialkyl groups, aryl groups, heteroaromatic groups, ethylenically unsaturated hydrocarbon groups, acetylenically unsaturated hydrocarbon groups, ketonic groups, and aromatic organometallic moieties, is provided. When combined with a compound comprising a metal from Groups IIIB to VIII or the Lanthanide series of the Periodic Table of elements and an activating cocatalyst, the catalyst precursor is useful for the polymerization of olefins.

7 Claims, No Drawings

OLEFIN POLYMERIZATION METHOD COMPRISING ALLYL-CYCLOALKADIENYL DIANIONS AS CATALYST PRECURSORS

This application is a Division of prior U.S. application Ser. No. 08/536,947 Filing Date Sep. 29, 1995, now U.S. Pat. No. 5,700,748.

The invention relates to a novel family of conjugated allyl-cycloalkadienyl dianions useful as catalyst precursors for the production of olefin polymers, such as polymers of ethylene, higher alpha-olefins, dienes, and mixtures thereof.

BACKGROUND

Recently, single site catalysts have been developed to prepare olefin polymers. Typically, single site catalysts are metallocenes, organometallic coordination complexes containing one or more π-bonded moieties in association with a metal atom from Groups IIIB to VIII or the Lanthanide series of the Periodic Table of Elements. Catalyst compositions containing single site catalysts are reportedly highly useful in the preparation of polyolefins, producing homogeneous polymers at excellent polymerization rates and allowing one to tailor closely the final properties of the polymer as desired.

European Patent Application Nos. 0 586 167 A1 and 0 586 168 A1 relate to polyolefin catalyst compositions comprising metallocene complexes of the formula

or

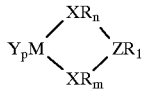

wherein R is a hydrocarbyl optionally containing oxygen, silicon, phosphorous, nitrogen, or boron atoms, X is an organic group containing a cyclopentadienyl nucleus, M is a Group IVA metal, Y is a univalent anionic ligand, and Z is a bridging group. According to these applications, at least one R group must contain a polymerizable group, preferably containing at least three carbon atoms. Preferred metallocene complexes are zirconium complexes in which the polymerizable group is vinyl. Compounds such as

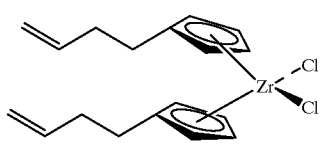

are disclosed.

German Patent Application No. 3840772 A1 relates to metallocene catalyst components for use in polymerizing olefins prepared by reacting a zirconium, titanium, or hafnium metallocene compound with a poly(methhydrogensiloxane) in the presence of a hydrosilation catalyst. Compounds such as

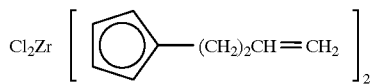

are disclosed.

A new single site, olefin polymerization catalyst composition is described herein having good polymerization activity and productivity, which is easily and inexpensively prepared. The catalyst composition comprises the reaction product of 1) a conjugated allyl-cycloalkadienyl dianion catalyst precursor, 2) a compound comprising a metal from Groups IIIB to VIII or the Lanthanide series, and 3) an activating cocatalyst.

SUMMARY OF THE INVENTION

The invention provides a catalyst precursor of the formula:

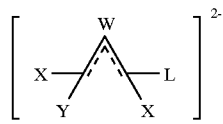

wherein:

L is a cycloalkadienyl ligand;

W, X, Y, and Z are independently hydrogen, a hydrocarbyl group containing 1 to 20 carbon atoms, or a silyl group, and may be connected to L through a bridging group comprising at least two Group IVA atoms; with the proviso that one of X, Y, and Z is a negative charge stabilizing group selected from Group IVA trialkyl groups, aryl groups, heteroaromatic groups, ethylenically unsaturated hydrocarbon groups, acetylenically unsaturated hydrocarbon groups, ketonic groups, and aromatic organometallic moieties.

The invention also provides a catalyst composition comprising the reaction product of the above catalyst precursor, a compound comprising a metal from Groups IIIB to VIII or the Lanthanide series, and an activating cocatalyst.

The invention further provides a process for the production of an olefin polymer, which comprises contacting an olefin monomer under polymerization conditions with the above catalyst composition, as well as olefin polymers, such as ethylene polymers, produced by this process.

DETAILED DESCRIPTION OF THE INVENTION

The catalyst precursor is a conjugated allyl-cycloalkadienyl dianion having the formula:

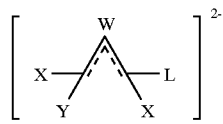

In the formula above, L is a cycloalkadienyl ligand, such as cyclopentadienyl, indenyl, or fluorenyl, that may be unsubstituted or substituted with one or more hydrocarbyl groups such as alkyl, aryl, alkylaryl, or arylalkyl, silyl groups, and the like. Preferably, L is an unsubstituted or substituted cyclopentadienyl or indenyl ligand.

Except as provided in the next paragraph, W, X, Y, and Z are independently hydrogen, a hydrocarbyl group containing 1 to 20 carbon atoms, or a silyl group. One or more of W, X, Y, and Z may be connected to L through bridging groups comprising two or more Group IVA atoms.

It is necessary that one of X, Y, and Z is a negative charge stabilizing group. Examples of negative charge stabilizing groups are Group IVA trialkyl groups, aryl groups, heteroaromatic groups, ethylenically unsaturated hydrocarbon groups, acetylenically unsaturated hydrocarbon groups, ketonic groups, and aromatic organometallic moieties.

Group IVA trialkyl groups have the formula (Group IVA element)($R_3$) wherein R is an alkyl group containing 1 to about 20 carbon atoms such as silyl, stannyl, germyl, or plumbyl.

Examples of aryl groups are phenyl, naphthyl, biphenyl, anthracenyl, and substituted phenyl groups such as tolyl, methoxyphenyl, and ortho-t-butyl-phenyl.

Examples of heteroaromatic groups are pyridyl, furyl, pyrryl, and thienyl.

Examples of ethylenically unsaturated hydrocarbon groups are vinyl groups, substituted vinyl groups, allenic groups, substituted allenic groups, dienyl groups, and substituted dienyl groups.

Examples of acetylenically unsaturated hydrocarbon groups are phenylalkynyl, trimethyl-silylalkynyl, propynyl, hexynyl, and 3-3-dimethylbutynyl.

Examples of ketonic groups are benzoyl and pivaloyl.

Examples of aromatic organometallic moieties are ferrocene, titanocene, chromocene and vanadocene.

Preferred negative charge stabilizing groups are aryl groups, particularly phenyl.

The catalyst precursor may be in the form of a monomer, a dimer, an oligomer, or polymer.

In a preferred embodiment of the invention, the catalyst precursor is a cinnamyl-cyclopentadienyl dianion of the formula:

including any isomers thereof.

In another preferred embodiment of the invention, the catalyst precursor is a cinnamyl-indenyl dianion of the formula:

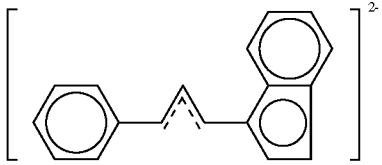

including any isomers thereof.

The catalyst precursor may be made by any synthesis method, and the method of making the catalyst precursor is not critical to the invention. One useful method of making the catalyst precursor is by contacting a cycloalkadienyl-containing salt with an allyl-containing halogen compound, and metallating the resulting product with a metallating reagent, preferably an alkyllithium compound such as methyllithium or n-butyllithium. Contacting may be performed at atmospheric pressures and temperatures in the range of about −78° C. to room temperature, preferably in the range of −30° C. to room temperature.

For example, when making the preferred cinnamyl-cyclopentadienyl dianion catalyst precursor, sodium cyclopentadienide may be reacted with cinnamylchloride or cinnamylbromide. The product, cinnamylcyclopentadiene may then be metallated with an equivalent of n-butyllithium in a suitable solvent to form the mono-anion, cinnamyl-cyclopentadienide (as the mono lithium salt). Examples of useful solvents are ethers such as tetrahydrofuran (THF), mono-, di-, tri-, and tetraglymes, and methyl t-butyl ether (MTBE), chelating amines such as N,N,N',N'-tetramethyl ethylenediamine, and amides such as hexamethylphosphoramide. The mono-anion may then be converted to the cinnamyl-cyclopentadienyl dianion via a second metallation with a second equivalent of n-butyllithium in solvent. Alternatively, one can convert the cinnamylcyclopentadiene directly to the cinnamyl-cyclopentadienyl dianion catalyst precursor in a one-pot synthesis by sequentially adding to the sodium cyclopentadienide the cinnamylchloride or cinnamylbromide and two equivalents of alkyllithium compound.

The catalyst composition comprises the reaction product of the conjugated allyl-cycloalkadienyl dianion catalyst precursor, a compound comprising a metal from Groups IIIB to VIII or the Lanthanide series (also referred to herein as "the metal compound"), and an activating cocatalyst. In forming the reaction product, the catalyst precursor (which may be in the form of a salt containing the conjugated allyl-cycloalkadienyl dianion and metal cation from the metallating reagent), the metal compound, and the activating cocatalyst are contacted at a temperature in the range of about −78° C. to room temperature, preferably in the range of about −30° C. to room temperature, at atmospheric pressure. Contacting is preferably done in the presence of a suitable solvent, i.e., an ether such as THF or a hydrocarbon such as hexane or toluene. The catalyst precursor, metal compound, and activating cocatalyst may be contacted in any order; however, it is preferred that either the catalyst precursor and metal compound be contacted first, followed by contacting with the activating cocatalyst, or the catalyst presursor and activating cocatalyst be contacted first, followed by contacting the metal compound.

When the catalyst precursor is contacted first with the activating cocatalyst, it may be desirable to add further activating cocatalyst to the reaction product after the metal compound has been added in order to adjust the overall ratio of activating cocatalyst to metal in the catalyst composition.

The compound comprising a metal from Groups IIIB to VIII or the Lanthanide series is preferably a compound containing a Group IVB metal. More preferably, the metal compound is a zirconium compound. Suitable zirconium compounds include zirconium halides, zirconium alkyl halides, zirconium alkyls, zirconium amides, zirconium diketonates, zirconium alkoxides, zirconium carboxylates, and the like. Specific examples of zirconium compounds include zirconium tetrachloride, cyclopentadienyl zirconium trichloride, pentamethylcyclopentadienyl zirconium trichloride, tetrabenzylzirconium, tetrakis(diethylamino) zirconium, zirconium acetylacetonate, zirconium hexafluoroacetoacetonate, bis(acetylacetonate) zirconium dichloride, zirconium isopropoxide, zirconium 2-ethylhexanoate, $ClZr[CH(SiMe_3)_2]_3$, $[Me_3SiCH_2]_2ZrCl_2 (Et_2O)_2$, $[PhCH_2]_2ZrCl_2$, $(Me_3CH_2)_2ZrCl_2$, $(Et_2O)_2$, and $[ZrCl_2(THF)(eta-C_8H_8)]$.

When the catalyst precursor has been synthesized with a strong metallating reagent, such as an alkyllithium compound, it may be useful to contact the catalyst precursor with a transmetallating compound before the catalyst precursor is contacted with the metal compound. The transmetallating compound, which is preferably a Group IIA, IIB, IIIA, or IVA halide or alkoxide, removes the metal cation (from the metallating reagent) associated with the catalyst precursor and replaces it with a more reactive metal. This in turn facilitates reaction of the catalyst precursor with the metal compound. Particularly preferred transmetallating compounds are silicon, aluminum, and tin halides and alkoxides.

The activating cocatalyst is capable of activating the catalyst composition. Preferably, the activating cocatalyst is one of the following: (a) branched or cyclic oligomeric poly(hydrocarbylaluminum oxide)s which contain repeating units of the general formula —(Al(R*)O)—, where R* is hydrogen, an alkyl radical containing from 1 to about 12 carbon atoms, or an aryl radical such as a substituted or unsubstituted phenyl or naphthyl group; (b) ionic salts of the general formula [A$^+$][BR$_4^-$], where A$^+$ is a cationic Lewis or Bronsted acid capable of abstracting an alkyl, halogen, or hydrogen from the metallocene catalysts, B is boron, and R is a substituted aromatic hydrocarbon, preferably a perfluorophenyl radical; (c) boron alkyls of the general formula BR$_3$, where R is as defined above; or mixtures thereof.

If an ionic salt of the formula [A$^+$][BR**$_4^-$] or a boron alkyl is used as the activating cocatalyst, it may be desirable to contact the metal compound with an aluminum alkyl such as trimethylaluminum or triisobutylaluminum, in order to alkylate the metal compound before it is contacted with the catalyst precursor and activating cocatalyst.

Preferably, the activating cocatalyst is a branched or cyclic oligomeric poly(hydrocarbylaluminum oxide) or a boron alkyl. More preferably, the activating cocatalyst is an aluminoxane such as methylaluminoxane (MAO) or modified methylaluminoxane (MMAO), or a boron alkyl.

Aluminoxanes are well known in the art and comprise oligomeric linear alkyl aluminoxanes represented by the formula:

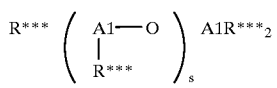

and oligomeric cyclic alkyl aluminoxanes of the formula:

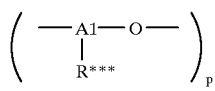

wherein s is 1–40, preferably 10–20; p is 3–40, preferably 3–20; and R*** is an alkyl group containing 1 to 12 carbon atoms, preferably methyl or an aryl radical such as a substituted or unsubstituted phenyl or naphthyl radical.

Aluminoxanes may be prepared in a variety of ways. Generally, a mixture of linear and cyclic aluminoxanes is obtained in the preparation of aluminoxanes from, for example, trimethylaluminum and water. For example, an aluminum alkyl may be treated with water in the form of a moist solvent. Alternatively, an aluminum alkyl, such as trimethylaluminum, may be contacted with a hydrated salt, such as hydrated ferrous sulfate. The latter method comprises treating a dilute solution of trimethylaluminum in, for example, toluene with a suspension of ferrous sulfate heptahydrate. It is also possible to form methylaluminoxanes by the reaction of a tetraalkyldialuminoxane containing C$_2$ or higher alkyl groups with an amount of trimethylaluminum that is less than a stoichiometric excess. The synthesis of methylaluminoxanes may also be achieved by the reaction of a trialkyl aluminum compound or a tetraalkyldialuminoxane containing C$_2$ or higher alkyl groups with water to form a polyalkyl aluminoxane, which is then reacted with trimethylaluminum. Further modified methylaluminoxanes, which contain both methyl groups and higher alkyl groups, may be synthesized by the reaction of a polyalkyl aluminoxane containing C$_2$ or higher alkyl groups with trimethylaluminum and then with water as disclosed in, for example, U.S. Pat. No. 5,041,584.

The amounts of catalyst precursor, metal compound, and activating cocatalyst usefully employed in the catalyst composition may vary. Generally, the ratio of catalyst precursor to metal compound may range from about 1:5 to about 5:1, preferably from about 1:3 to about 3:1, more preferably from about 1:2 to about 2:1.

When the activating cocatalyst is a branched or cyclic oligomeric poly(hydrocarbylaluminum oxide), the mole ratio of aluminum atoms contained in the poly (hydrocarbylaluminum oxide) to total metal atoms contained in the metal compound is generally in the range of from about 2:1 to about 100,000:1, preferably in the range of from about 10:1 to about 10,000:1, and most preferably in the range of from about 50:1 to about 2,000:1. When the activating cocatalyst is an ionic salt of the formula [A$^+$][BR$_4^-$] or a boron alkyl of the formula BR$_3$, the mole ratio of boron atoms contained in the ionic salt or the boron alkyl to total metal atoms contained in the metal compound is generally in the range of from about 0.5:1 to about 10:1, preferably in the range of from about 1:1 to about 5:1.

The catalyst composition may be supported or unsupported, or may be spray dried with or without filler. In the case of a supported catalyst composition, the catalyst composition may be impregnated in or deposited on the surface of an inert substrate such as silicon dioxide, aluminum oxide, magnesium dichloride, polystyrene, polyethylene, polypropylene, or polycarbonate, such that the catalyst composition is between 1 and 90 percent by weight of the total weight of the catalyst composition and the support.

The catalyst composition may be used for the polymerization of olefins by any suspension, solution, slurry, or gas phase process, using known equipment and reaction conditions, and is not limited to any specific type of reaction system. Generally, olefin polymerization temperatures range from about 0° C. to about 200° C. at atmospheric, subatmospheric, or superatmospheric pressures. Slurry or solution polymerization processes may utilize subatmospheric or superatmospheric pressures and temperatures in the range of about 40° C. to about 110° C. A useful liquid phase polymerization reaction system is described in U.S. Pat. No. 3,324,095. Liquid phase reaction systems generally comprise a reactor vessel to which olefin monomer and catalyst composition are added, and which contains a liquid reaction medium for dissolving or suspending the polyolefin. The liquid reaction medium may consist of the bulk liquid monomer or an inert liquid hydrocarbon that is nonreactive under the polymerization conditions employed. Although such an inert liquid hydrocarbon need not function as a solvent for the catalyst composition or the polymer obtained by the process, it usually serves as solvent for the monomers employed in the polymerization. Among the inert liquid hydrocarbons suitable for this purpose are isopentane, hexane, cyclohexane, heptane, benzene, toluene, and the like. Reactive contact between the olefin monomer and the catalyst composition should be maintained by constant stirring or agitation. The reaction medium containing the olefin polymer product and unreacted olefin monomer is withdrawn from the reactor continuously. The olefin polymer product is separated, and the unreacted olefin monomer and liquid reaction medium are recycled into the reactor.

Preferably, gas phase polymerization is employed, with superatmospheric pressures in the range of 1 to 1000 psi, preferably 50 to 400 psi, most preferably 100 to 300 psi, and temperatures in the range of 30 to 130° C., preferably 65 to 110° C. Stirred or fluidized bed gas phase reaction systems are particularly useful. Generally, a conventional gas phase, fluidized bed process is conducted by passing a stream containing one or more olefin monomers continuously through a fluidized bed reactor under reaction conditions and in the presence of catalyst composition at a velocity sufficient to maintain a bed of solid particles in a suspended condition. A stream containing unreacted monomer is withdrawn from the reactor continuously, compressed, cooled and recycled into the reactor. Product is withdrawn from the reactor and make-up monomer is added to the recycle stream. As desired for temperature control of the system, any gas inert to the catalyst composition and reactants may also be present in the gas stream. In addition, a fluidization aid such as carbon black, silica, clay, or talc may be used, as disclosed in U.S. Pat. No. 4,994,534.

Polymerization may be carried out in a single reactor or in two or more reactors in series, and is conducted substantially in the absence of catalyst poisons. Organometallic compounds may be employed as scavenging agents for poisons to increase the catalyst activity. Examples of scavenging agents are metal alkyls, preferably aluminum alkyls, most preferably triisobutylaluminum.

Conventional adjuvants may be included in the process, provided they do not interfere with the operation of the catalyst composition in forming the desired polyolefin. Hydrogen may be used as a chain transfer agent in the process, in amounts up to about 10 moles of hydrogen per mole of total monomer feed.

Olefin polymers that may be produced according to the invention include, but are not limited to, ethylene homopolymers, homopolymers of linear or branched higher alpha-olefins containing 3 to about 20 carbon atoms, and interpolymers of ethylene and such higher alpha-olefins, with densities ranging from about 0.86 to about 0.95. Suitable higher alpha-olefins include, for example, propylene, 1-butene, 1-pentene, 1-hexene, 4-methyl-1-pentene, 1-octene, and 3,5,5-trimethyl-1-hexene. Olefin polymers according to the invention may also be based on or contain conjugated or non-conjugated dienes, such as linear, branched, or cyclic hydrocarbon dienes having from about 4 to about 20, preferably 4 to 12, carbon atoms. Preferred dienes include 1,4-pentadiene, 1,5-hexadiene, 5-vinyl-2-norbornene, 1,7-octadiene, vinyl cyclohexene, dicyclopentadiene, butadiene, isobutylene, isoprene, ethylidene norbornene and the like. Aromatic compounds having vinyl unsaturation such as styrene and substituted styrenes, and polar vinyl monomers such as acrylonitrile, maleic acid esters, vinyl acetate, acrylate esters, methacrylate esters, vinyl trialkyl silanes and the like may be polymerized according to the invention as well. Specific olefin polymers that may be made according to the invention include, for example, polyethylene, polypropylene, ethylene/propylene rubbers (EPR's), ethylene/propylene/diene terpolymers (EPDM's), polybutadiene, polyisoprene and the like.

The following examples further illustrate the invention.

EXAMPLES

Glossary

Activity is measured in kg polyethylene/mmol Zr·hr·100 psi ethylene.

I2 is melt index (dg/min), measured using ASTM D-1238 Condition E at 190° C.

I21 is flow index (dg/min), measured using ASTM D-1238-Condition F.

MFR is Melt Flow Ratio, I21/I2.

MMAO is a solution of modified methylaluminoxane in heptane, approximately 1.9 molar in aluminum, commercially available from Akzo Chemicals, Inc. (type 3).

BBF is Butyl Branching Frequency, number of butyl branches per 1000 main chain carbon atoms.

$M_W$ is Weight Average Molecular Weight, as determined by gel permeation chromatography using crosslinked polystyrene columns; pore size sequence: 1 column less than 1000 Å, 3 columns of mixed $5\times10^7$ Å; 1,2,4-trichlorobenzene solvent at 140° C. with refractive index detection.

PDI is Polydispersity Index, equivalent to Molecular Weight Distribution ($M_w/M_n$).

Examples 1–10

Catalyst compositions comprising the reaction products of cinnamyl-cyclopentadienyl dianion, modified methylaluminoxane, and various zirconium compounds were prepared and used to copolymerize ethylene and 1-hexene as follows.

Preparation and Isolation of Cinnamyl-Cyclopentadienyl Dianion

A solution of cinnamyl bromide (102 mmoles) in 95 ml of THF was cooled to 0° C. An equimolar amount of sodium cyclopentadienide (2.0M in THF) was slowly added to the chilled solution under argon. After the addition, the reaction to cinnamyl cyclopentadiene was complete according to GC analysis. The reaction mixture was concentrated down to a residue under vacuum yielding a brownish oil.

The cinnamyl cyclopentadiene residue (102 mmoles) was then placed under argon, dilluted with 100 ml of ether, and stirred. The mixture was then vacuum-filtered in an oven-dried, double-ended flit (to remove the sodium bromide) and solids were washed with ether. The filtrate was placed under argon and cooled to −78° C. To the solution was added 0.6 equivalents of n-butyllithium (3.089M in hexanes, 19.4 ml, 60 mmoles). The mixture was allowed to stir overnight. The solid, monoanion product was vacuum-filtered using a dry, double-ended frit and washed with dry ether. The solids were vacuum-dried and stored in a dry box.

A solution of the resulting lithium cinnamylcyclopentadienide in THF was placed under argon. To it was added 3 equivalents of methyllithium (in ether) at room temperature. The resulting solution was stirred for two hours at room temperature, and then concentrated down to a residue under strong vacuum. To the residue was added dry ether, and result was filtered to yield the dianion as the dilithium salt.

Preparation of Catalyst Compositions

A series of catalyst compositions were then made by reacting the cinnamyl-cyclopentadienyl dianion (as the dilithium salt) prepared above with zirconium tetrachloride, cyclopentadienyl zirconium trichloride (CpZrCl₃), or pentamethylcyclopentadienyl zirconium trichloride (Cp*ZrCl₃), and MMAO, as follows.

Equimolar amounts of dilithium cinnamyl cyclopentadienide and zirconium compound were charged to a flask in a dry-box. To this mixture, with stirring, was added approximately 1 mL of an ether, either chilled or at room temperature, as indicated in Table 1. The resulting mixture was concentrated to a residue under vacuum.

In the case of Examples 6 and 10, the flask was first removed from the box, chilled in a low temperature bath (−78° C.) and with stirring treated with 10 ml of ether. The mixture was then allowed to warm slowly to room temperature overnight, and then concentrated to a residue under vacuum.

For each Example, the resulting dianion/zirconium complex was then dissolved in dry toluene. In Examples 4, 5, 9, and 10, 500 equivalents of MMAO were charged to an oven dried, glass vial under stirring, and the toluene solution of dianion/zirconium complex was added thereto. In Examples 1, 2, 3, 7, and 8, 10 mL of toluene was first charged to the vial before the introduction of MMAO. In Example 6, the dianion/zirconium complex was charged to the vial, 10 mL of toluene was added under stirring, and then 500 equivalents of MMAO were added to the vial. Catalyst compositions having MMAO/zirconium mole ratios of 1000 were formed in each case.

Polymerization

Polymerizations using these catalyst compositions were conducted in the slurry phase in a one liter, stainless steel autoclave equipped with a mechanical agitator. Reactions were run at 75° C. under 85 psia of ethylene, with 43 mls of 1-hexene and 600 mL of hexane solvent also present to the reactor. Reaction times were each 30 minutes.

The results are shown in Table 1.

Examples 11–16

Further catalyst compositions comprising the reaction products of cinnamyl-cyclopentadienyl dianion, modified methylaluminoxane, and various zirconium compounds were prepared and used to copolymerize ethylene and 1-hexene as described above in Examples 1–10. The results are shown in Table 2.

Examples 17–24

Further catalyst compositions comprising the reaction products of cinnamyl-cyclopentadienyl dianion, modified methylaluminoxane, and various zirconium compounds were prepared and used to copolymerize ethylene and 1-hexene as follows.

Preparation of Catalyst Compositions

For each of Examples 17–24, cinnamyl-cyclopentadienyl dianion (0.0452 mmoles) as prepared in Examples 1–10 was combined with 1.5 mL of MMAO at room temperature and stirred for four days. Approximately 5 μmoles of the resulting dianion/MMAO complex was added to an oven dried vial containing approximately 5 μmoles of zirconium compound shown in Table 3 (except in the case of Examples 22 and 23, in which only approximately 2.5 μmoles of zirconium compound were used). In the case of Examples 17, 18, 20, 21 and 22, toluene was also added to the vial. The resulting mixture was stirred for 20 to 55 minutes to form the catalyst composition.

Polymerization

For each of Examples 17–24, the catalyst composition was introduced into the autoclave reactor, with an additional 2 mmoles of MMAO (except in the case of Examples 22 and 23, in which 1 mmole and 0.33 mmoles, respectively, were additionally used). Referring to Table 3 below, polymerizations using these catalyst compositions were conducted as in Examples 1–10.

Example 25

A catalyst composition comprising the reaction product of 1-cinnamylindenyl dianion, modified methylaluminoxane, and $ZrCl_4$ was prepared and used to copolymerize ethylene and 1-hexene as follows.

Preparation of 1-Cinnamylindenyl Dianion

A solution of 98% indene (364 mmoles) in 300 ml of THF was cooled to −78° C. under argon. An equimolar amount of n-butyllithium was added to the solution. The resulting mixture was allowed to warm to room temperature. It was then charged to an equimolar amount of 95% cinnamyl chloride (58.45 g) in 100 ml of THF at −30° C. The mixture was then allowed to warm to room temperature and react for one hour to form cinnamyl indene. The cinnamyl indene was concentrated down to a residue under strong vacuum, and then washed and concentrated twice with 100 ml of hexane. The residue was washed a third time with 100 ml of warm hexane and filtered while hot. The filtrate was again concentrated down to a residue under vacuum. The cinnamyl indene filtrate melted at 55–69° C. Recovery yield was 62%.

A solution of the cinnamyl indene (224 mmoles) in 300 ml of ether was placed under argon, and cooled to 0° C. To the solution was added 0.89 equivalents (200 mmoles) of n-butyllithium, after which the solution was allowed to warm to room temperature. Hexane was added to the mixture, and it was concentrated down almost to a residue. More hexane was added to the mixture and it was allowed to stir overnight. The product, solid lithium cinnamyl indenide, was later filtered, washed, and vacuum-dried. The recovery yield was 44 g.

To generate the dianion, a solution of the lithium cinnamyl indenide (11 mmoles) in 50.0 ml of THF was placed under argon and cooled to 0° C. To it was fed 1.0 equivalent of butyllithium, followed by stirring at room temperature for one hour.

Preparation of Catalyst Composition

The dianion solution was then transferred by double-ended needle to a solution containing 2.0 equivalents of zirconium tetrachloride (5.0 g, 21.4 mmoles) in 50 ml of THF at −30° C., and stirred for three days. The reaction mixture was concentrated to a residue under vacuum and combined with 500 equivalents of MMAO in an oven dried, glass vial with stirring.

Polymerization

Copolymerization of ethylene and 1-hexene using the catalyst composition containing 1-cinnamylindenyl dianion was conducted as in Examples 1–10 above. The activity of the catalyst was 6,700. A copolymer was obtained having a butyl branching frequency of 11.9, an I2 of 0.513 and a melt flow ratio of 26.3.

Examples 26–29

Further catalyst compositions comprising reaction products of cinnamyl-cyclopentadienyl dianion, boron compounds, modified methylaluminoxane, and various zirconium compounds were prepared and used to copolymerize ethylene and 1-hexene as follows.

Preparation of Catalyst Compositions

In each of Examples 26–29, a solution of dilithium cinnamyl cyclopentadienide as prepared in Examples 1–10 above (0.28 mmoles) in THF was placed under argon and chilled to 0° C. An equimolar amount of boron compound as indicated in Table 4 was added to the solution. The resulting mixture was stirred for 30 minutes at 0° C., before warming to room temperature. It was then charged to a solution of zirconium compound as shown in Table 4 in THF at room temperature. The mixture was stirred overnight and then concentrated to a residue under vacuum.

For each of Examples 26–29, the resulting dianion/boron/zirconium complex was then dissolved in dry toluene. In Example 28, 500 equivalents of MMAO were charged to an oven dried, glass vial under stirring, and the toluene solution of dianion/boron/zirconium complex was added thereto. In Examples 26 and 27, 10 mL of toluene was first charged to the vial before the introduction of MMAO. In Example 29, the dianion/boron/zirconium complex was charged to the vial, 10 mL of toluene was added under stirring, and then 500 equivalents of MMAO were added to the vial.

Polymerization

Referring to Table 4 below, polymerizations using these catalyst compositions were conducted as in Examples 1–10 above.

Example 30

A catalyst composition comprising the reaction product of cinnamyl-cyclopentadienyl dianion transmetallated first with chlorotrimethyl silane, $ZrCl_4$ and modified methylaluminoxane was prepared and used to copolymerize ethylene and 1-hexene as follows.

A solution of dilithium cinnamyl cyclopentadienide as prepared in Examples 1–10 above (1.09 mmoles) in approximately 1 ml of THF was placed under argon. To it was charged 2.5 equivalents of chlorotrimethylsilane, followed by stirring for 1 hr. The mixture was concentrated down to a residue under vacuum. The residue was washed with toluene twice and vacuum-filtered to remove lithium chloride.

The filtrate was then charged to an equimolar amount of zirconium tetrachloride at room temperature and stirred. The mixture was concentrated to a residue under vacuum and combined with 500 equivalents of MMAO in an oven dried, glass vial with stirring.

Polymerization

Copolymerization of ethylene and 1-hexene using this catalyst composition was conducted as in Examples 1–10. The activity of the catalyst was 7,211. A copolymer was obtained having an I2 of 0.176, an I21 of 3.35 and a melt flow ratio of 22.05.

Example 31

A catalyst composition comprising the reaction product of cinnamyl-cyclopentadienyl dianion transmetallated first with trimethyltin chloride, $ZrCl_4$ and modified methylaluminoxane was prepared and used to copolymerize ethylene and 1-hexene as follows.

A solution of dilithium cinnamyl cyclopentadienide as prepared in Examples 1–10 above (0.2 mmoles) in 5.0 ml of THF was placed under argon and cooled to –78° C. To this was charged 1.0 equivalent of trimethyltin chloride and the resulting mixture was allowed to warm to room temperature. The mixture was concentrated to a residue under vacuum.

To form the catalyst composition, the resulting product was then charged to an equimolar amount of zirconium tetrachloride at room temperature, and stirred overnight. It was concentrated down to a residue under vacuum and combined with 500 equivalents of MMAO in an oven dried, glass vial with stirring.

Polymerization

Copolymerization of ethylene and 1-hexene using this catalyst composition was conducted as in Examples 1–10. The activity of the catalyst was 20,888. A copolymer was obtained having an I2 of 0.294, an I21 of 5.2, and a melt flow ratio of 17.6.

Example 32

A catalyst composition comprising the reaction product of cinnamyl-cyclopentadienyl dianion transmetallated first with trimethylaluminum, $ZrCl_4$ and modified methylaluminoxane was prepared and used to copolymerize ethylene and 1-hexene as follows.

A solution of dilithium cinnamyl cyclopentadienide as prepared in Examples 1–10 above (0.124 mmoles) in 5.0 ml of THF was placed under argon and cooled to –30° C. To it was charged 2.0 equivalents of trimethylaluminum. It was then warmed to room temperature and stirred for four hours. The mixture was concentrated down to a residue under strong vacuum.

The resulting product was then charged to 2 equivalents of zirconium tetrachloride at room temperature, and stirred for three days. It was concentrated down to a residue under vacuum and combined with 500 equivalents of MMAO in an oven dried, glass vial with stirring.

Polymerization

Copolymerization of ethylene and 1-hexene using this catalyst composition was conducted as in Examples 1–10. The activity of the catalyst was 12,205. A copolymer was obtained having an I2 of 0.166, an I21 of 3.08, a melt flow ratio of 18.5, and a BBF of 9.39.

Example 33

A catalyst composition comprising the reaction product of cinnamyl-cyclopentadienyl dianion transmetallated first with magnesium bromide, $ZrCl_4$ and modified methylaluminoxane was prepared and used to copolymerize ethylene and 1-hexene as follows.

An equimolar (0.22 mmoles) mixture of dilithium cinnamyl cyclopentadienide as prepared in Examples 1–10 above and magnesium bromide was stirred at room temperature in a dry box. To the solids was added about 1 ml of chilled (–30° C.) THF-d8. The solution was stirred for two hours.

The catalyst composition was prepared by first charging the resulting product to an equimolar solution of zirconium tetrabromide in approximately 1 ml of THF-d8, at room temperature. The mixture was stirred overnight. The solvent layer was concentrated down to a residue under vacuum. To the residue was added 10 mL of toluene under stirring, followed by 500 equivalents of MMAO.

Polymerization

Copolymerization of ethylene and 1-hexene using this catalyst composition was conducted as in Examples 1–10. The activity of the catalyst was 4,345.

TABLE 1

| Example | Ether, °C. | Zr Compound | Dianion/Zr Mole Ratio | Activity | BBF | $M_w$/PDI |
|---|---|---|---|---|---|---|
| 1 | THF, RT | $ZrCl_4$ | 2.0 | 38,325 | 13.9 | 208K/3.955 |
| 2 | THF, –30° | $ZrCl_4$ | 1.0 | 67,577 | 10.4 | 187K/3.264 |
| 3 | THF, RT | $ZrCl_4$ | 1.0 | 20,013 | 10.3 | 242K/2.91 |
| 4 | THF, –30° | $ZrCl_4$ | 0.5 | 13,998 | 10.9 | |
| 5 | THF, –30° | $ZrCl_4$ | 0.5 | 15,402 | 8.8 | |
| 6 | $Et_2O$, –78° | $CpZrCl_3$ | 1.0 | 34,067 | 13.0 | 143K/3.78 |
| 7 | THF, RT | $CpZrCl_3$ | 1.0 | 63,823 | 10.5 | 165K/3.44 |
| 8 | THF, RT | $Cp*ZrCl_3$ | 1.0 | 55,014 | 6.6 | 374K/4.97 |
| 9 | THF, –30° | $Cp*ZrCl_3$ | 1.0 | 44,690 | 5.3 | 338K/4.49 |
| 10 | $Et_2O$, –78° | $Cp*ZrCl_3$ | 1.0 | 61,025 | 3.6 | 317K/3.31 |

TABLE 2

| Example | Zr Compound | Activity | I2 | I21 | MFR |
|---|---|---|---|---|---|
| 11 | ZrCl₄ | 20,013 | .085 | 2.29 | 27.05 |
| 12[1] | ZrCl₄ | 67,577 | .26 | 8.04 | 30.91 |
| 13[2] | CpZrCl₃ | 27,420 | .179 | 3.62 | 20.23 |
| 14 | CpZrCl₃ | 63,823 | .331 | 11.82 | 35.71 |
| 15[3] | ZrCl₄ | 38,325 | .189 | 7.99 | 42.23 |
| 16 | Cp*ZrCl₃ | 55,014 | <.1 | .559 | NA |

[1]contacting of dianion and zirconium compound at −30° C.
[2]dianion/Zr mole ratio was 2.
[3]dianion/Zr mole ratio was 0.5.

TABLE 3

| Example | Zr Compound | μmoles Zr Compound | Total Al/Zr Mole Ratio | Activity | BBF | M_w/PDI |
|---|---|---|---|---|---|---|
| 17 | ZrCl₄ | 5 | 500 | 9,320 | 8.5 | 174K/2.998 |
| 18 | (PhCH₂)₄Zr | 5 | 500 | 3,447 | | |
| 19 | Zr(NEt₂)₄ | 5 | 500 | 3,396 | | |
| 20 | CpZrCl₃ | 5 | 500 | 25,530 | 7.2 | 132K/3.307 |
| 21 | Cp*ZrCl₃ | 5 | 500 | 25,059 | | |
| 22 | Cp*ZrCl₃ | 2.5 | 500 | 61,421 | 6.3 | 240K/3.090 |
| 23 | Cp*ZrCl₃ | 2.5 | 200 | 8,208 | | |
| 24[1] | ZrCl₄ | 5 | 500 | 31,616 | 12.4 | |

[1]digested using 20 equivalents of MMAO.

TABLE 4

| Example | B and Zr Compounds | Activity | I2 | I21 | MFR |
|---|---|---|---|---|---|
| 26 | BPh₃, ZrCl₄ | 18,704 | <.1 | .899 | NA |
| 27 | BEt₃, ZrCl₄ | 9,921 | NA | NA | NA |
| 28 | BEt₃, ZrCl₄[1] | 53,289 | .152 | 3.35 | 22.05 |
| 29 | Ph₂BBr[1], ZrBr₄[1] | 14,337 | .202 | 375 | 18.54 |

[1]0.5 μmoles.

I claim:

1. A process for preparing an olefin polymer, which comprises contacting at least one olefin monomer under polymerization conditions with a catalyst composition comprising the reaction product of:
   1) a catalyst precursor of the formula:

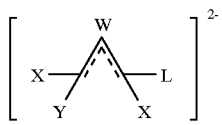

wherein:
   L is a cycloalkadienyl ligand;
   W, X, Y, and Z are independently hydrogen, a hydrocarbyl group containing 1 to 20 carbon atoms, or a silyl group, and may be connected to L through a bridging group comprising at least two Group IVA atoms; with the proviso that one of X, Y, and Z is a negative charge stabilizing group selected from the group consisting of Group IVA trialkyl groups, aryl groups, heteroaromatic groups, ethylenically unsaturated hydrocarbon groups, acetylenically unsaturated hydrocarbon groups, ketonic groups, and aromatic organometallic moieties;
   2) a compound comprising a metal from Groups IIIB to VIIIB or the Lanthanide series; and
   3) an activating cocatalyst.

2. The process of claim 1, wherein the catalyst precursor has the formula

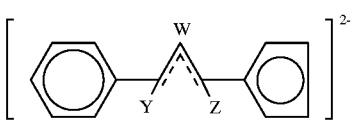

-continued

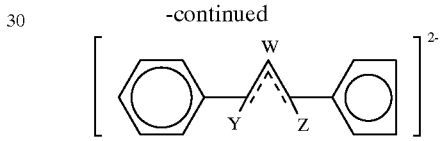

wherein W, Y and Z are each hydrogen.

3. The process of claim 1, wherein the catalyst precursor has the formula:

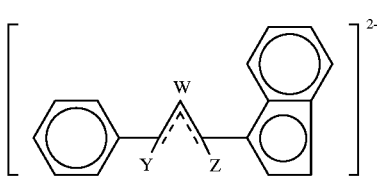

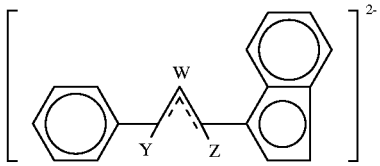

wherein W, Y and Z are each hydrogen.

4. The process of claim 1, wherein the compound comprising a metal from Groups IIIB to VIIIB or the Lanthanide series is a zirconium compound.

5. The process of claim 1, wherein the activating cocatalyst is selected from the group consisting of methylaluminoxane, modified methylaluminoxane, boron alkyls, and mixtures thereof.

6. The process of claim 1 performed in the gas phase.

7. The process of claim 1, wherein the olefin monomer is selected from the group consisting of ethylene, higher alpha-olefins, dienes, and mixtures thereof.

* * * * *